(12) United States Patent
Miyahara et al.

(10) Patent No.: US 10,819,960 B2
(45) Date of Patent: Oct. 27, 2020

(54) ENDOSCOPE

(71) Applicant: OLYMPUS CORPORATION, Tokyo (JP)

(72) Inventors: Hideharu Miyahara, Nagano (JP); Yusuke Nakagawa, Ina (JP); Kosuke Kawahara, Nagano (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/515,240

(22) Filed: Jul. 18, 2019

(65) Prior Publication Data

US 2020/0012085 A1 Jan. 9, 2020

Related U.S. Application Data

(63) Continuation of application No. PCT/JP2017/033883, filed on Sep. 20, 2017.

(30) Foreign Application Priority Data

Jan. 24, 2017 (WO) .................. PCT/JP2017/002354

(51) Int. Cl.
*A61B 1/00* (2006.01)
*A61B 1/05* (2006.01)
(Continued)

(52) U.S. Cl.
CPC ............... *H04N 7/22* (2013.01); *A61B 1/005* (2013.01); *A61B 1/0011* (2013.01);
(Continued)

(58) Field of Classification Search
CPC ... A61B 1/00013; A61B 1/05; A61B 1/00165; A61B 1/005; A61B 1/00096;
(Continued)

(56) References Cited

U.S. PATENT DOCUMENTS

2013/0169775 A1* 7/2013 Ono .................. A61B 1/128
348/68
2015/0086162 A1* 3/2015 Miyahara ........... G02B 23/2446
385/33
(Continued)

FOREIGN PATENT DOCUMENTS

EP 2947486 A1 11/2015
EP 3075298 A1 10/2016
(Continued)

OTHER PUBLICATIONS

International Search Report dated Oct. 17, 2017 issued in PCT/JP2017/033883.

*Primary Examiner* — Alison Slater
(74) *Attorney, Agent, or Firm* — Scully, Scott, Murphy & Presser, P.C.

(57) ABSTRACT

An endoscope including an image pickup module in a distal end section, wherein the image pickup module including an image pickup unit including an image pickup device, a light emitting element configured to emit an optical signal from a light emission surface, and a ferrule disposed in the image pickup unit, in which the light emission surface is inclined at a first angle of not less than 35 degrees nor more than 55 degrees to the distal end section central axis, a fiber distal end portion is inclined at a second angle of not less than 35 degrees nor more than 55 degrees to the distal end section central axis, and the optical fiber extends toward the distal end section central axis, and is arranged along a bending section central axis in a bending section.

20 Claims, 14 Drawing Sheets

(51) Int. Cl.
*A61B 1/005* (2006.01)
*A61B 1/04* (2006.01)
*G02B 6/42* (2006.01)
*G02B 23/24* (2006.01)
*G02B 23/26* (2006.01)
*H01S 5/022* (2006.01)
*H04N 7/18* (2006.01)
*H04N 7/22* (2006.01)
*H01L 31/0232* (2014.01)
*H04B 10/25* (2013.01)
*A61B 1/045* (2006.01)
*H04N 5/225* (2006.01)

(52) U.S. Cl.
CPC ...... *A61B 1/00013* (2013.01); *A61B 1/00096* (2013.01); *A61B 1/00124* (2013.01); *A61B 1/00165* (2013.01); *A61B 1/045* (2013.01); *G02B 6/424* (2013.01); *G02B 6/4212* (2013.01); *G02B 23/2446* (2013.01); *G02B 23/2484* (2013.01); *H04N 5/2253* (2013.01); *H04N 5/2254* (2013.01); *H04N 5/2256* (2013.01); *H04N 7/183* (2013.01)

(58) Field of Classification Search
CPC ......... A61B 1/0011; A61B 1/012; A61B 1/00; A61B 1/00126; A61B 1/0017; A61B 1/00117; A61B 1/00167; A61B 1/06; A61B 1/07; A61B 90/361; G02B 6/4202; G02B 23/2484; G02B 23/2469; G02B 6/424; G02B 23/26; G02B 6/4259; G02B 6/4281; G02B 6/42; G02B 6/423; G02B 6/4243; G02B 6/4257; G02B 6/428; G02B 6/262; H04N 2005/2255; H04N 5/2256; H04N 2/2253; H04N 7/183; H04N 7/22; H04N 5/2254; H04N 5/2251; H01S 5/02284; H01S 5/02252
See application file for complete search history.

(56) References Cited

U.S. PATENT DOCUMENTS

2015/0318924 A1  11/2015  Motohara
2016/0262599 A1   9/2016  Nakagawa

FOREIGN PATENT DOCUMENTS

| JP | 2013-025092 A | 2/2013 |
| JP | 2014137584 A | 7/2014 |
| JP | 2015-68835 A | 4/2015 |
| JP | 2015-97588 A | 5/2015 |
| JP | 2015097589 A | 5/2015 |
| JP | 2015-104387 A | 6/2015 |
| WO | WO 2014/112461 A1 | 7/2014 |
| WO | WO 2015-079780 A1 | 6/2015 |
| WO | WO 2016/189691 A1 | 12/2016 |

* cited by examiner

ENDOSCOPE

CROSS REFERENCE TO RELATED APPLICATION

This application is a continuation application of PCT/JP2017/033883 filed on Sep. 20, 2017 and claims benefit of International Application No. PCT/JP2017/002354 filed on Jan. 24, 2017, the entire contents of which are incorporated herein by this reference.

BACKGROUND OF THE INVENTION

1. Field of the Invention

The present invention relates to an endoscope in which an optical fiber configured to transmit an optical signal to be emitted by an optical module disposed in a rigid distal end section is inserted through an insertion section.

2. Description of the Related Art

An endoscope includes an image pickup device such as a CCD in a distal end section in an elongated insertion section. In recent years, an image pickup device having a large number of pixels has been studied to display a high-quality image. When the image pickup device having a large number of pixels is used, an amount of an image signal to be transmitted to a signal processor from the image pickup device increases. Accordingly, in electric signal transmission via a metal wiring by an electric signal, a wire diameter of the metal wiring needs to be increased to transmit a required signal amount, so that the insertion section may be thick due to the wiring.

To reduce the insertion section in diameter to make the endoscope minimally invasive, optical signal transmission via a thin optical fiber by an optical signal instead of the electric signal is preferable. For the optical signal transmission, an E/O-type optical module (electrical/optical converter) configured to convert an electric signal into an optical signal and an O/E-type optical module (optical/electrical converter) configured to convert an optical signal into an electric signal are used.

Japanese Patent Application Laid-Open No. 2013-025092 discloses an optical module including an optical element configured to input or output an optical signal, a substrate on which the optical element is mounted, and a holding section (ferrule) having a through hole into which an optical fiber configured to transmit the optical signal to be inputted into or outputted from the optical element is inserted.

Japanese Patent Application Laid-Open No. 2015-97589 discloses an endoscope in which no stress is applied to an optical fiber even if a bending section is deformed because the optical fiber is inserted through a center of the bending section.

SUMMARY OF THE INVENTION

An endoscope according to an embodiment of the present invention is an endoscope including an insertion section including a rigid distal end section, a bending section, and a flexible section consecutively connected to one another, an image pickup module configured to emit an optical signal being disposed in the rigid distal end section in the insertion section, in which the image pickup module includes an image pickup optical system an optical axis of which is parallel to a distal end section central axis of the rigid distal end section and is eccentric from the distal end section central axis, an image pickup unit including an image pickup device including a light receiving surface for receiving light of an object image collected by the image pickup optical system and a rear surface, a light emitting element configured to convert an image pickup signal outputted by the image pickup device into the optical signal and emit the optical signal from a light emission surface, an optical fiber configured to transmit the optical signal, and a ferrule including an insertion hole and disposed in the image pickup unit at a position where the optical fiber inserted into the insertion hole is optically coupled to the light emitting element, the light emission surface in the light emitting element is inclined at a first angle of not less than 35 degrees nor more than 55 degrees to the distal end section central axis, and the optical fiber has a fiber distal end portion, which is inserted into the insertion hole in the ferrule, inclined at a second angle of not less than 35 degrees nor more than 55 degrees to the distal end section central axis, extends toward the distal end section central axis, and is arranged along a bending section central axis in the bending section.

DETAILED DESCRIPTION OF THE PREFERRED EMBODIMENTS

First Embodiment

Figure 1:
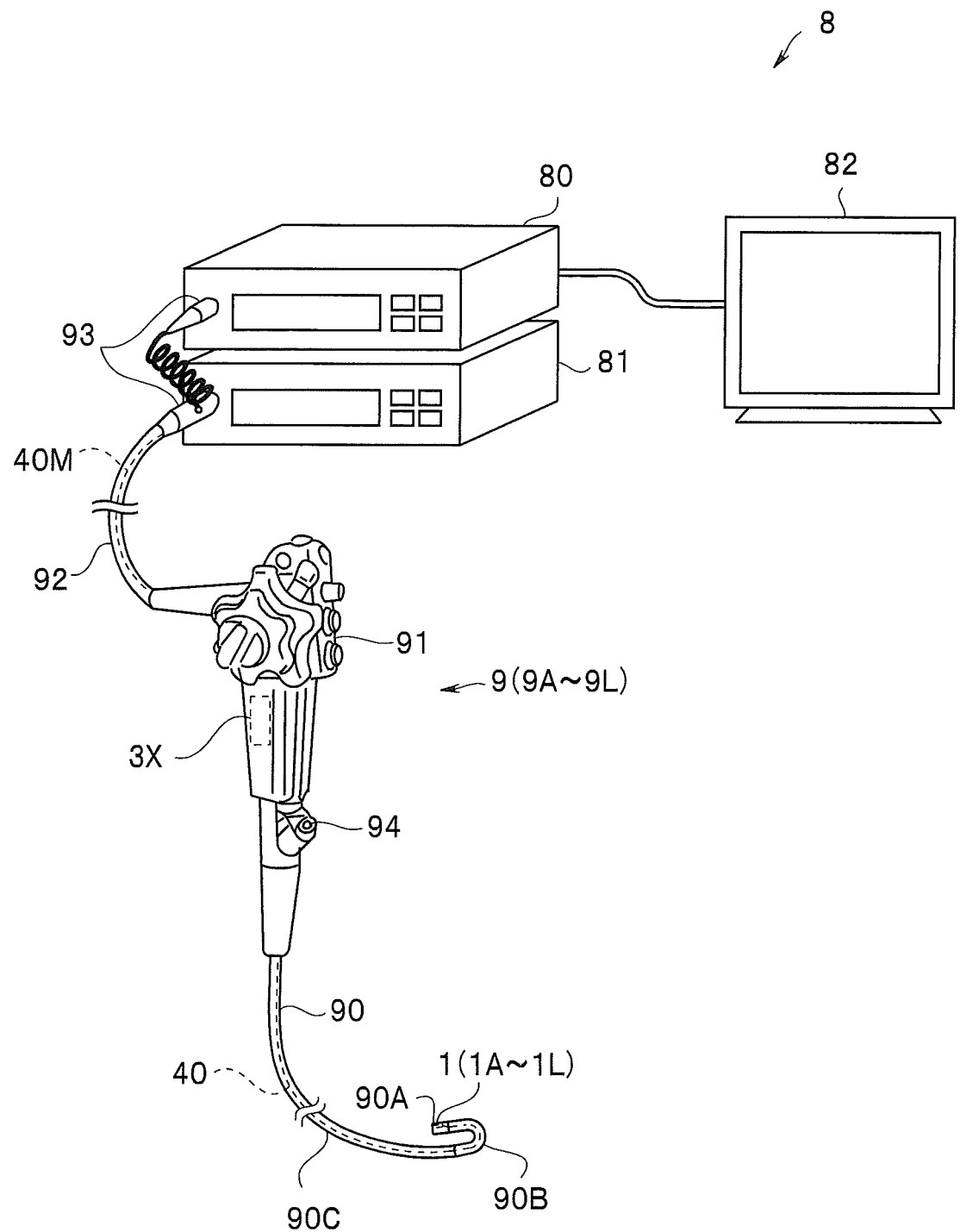
FIG. 1 is a perspective view of an endoscope system including an endoscope according to a first embodiment.

As illustrated in FIG. 1, an endoscope system 8 including an endoscope 9 according to the present embodiment includes the endoscope 9, a processor 80, a light source device 81, and a monitor 82. For example, the endoscope 9 shoots an in-vivo image of a subject and outputs an image pickup signal with an insertion section 90 circular in cross section inserted into a body cavity of the subject.

Note that in the following description, drawings based on each of embodiments are schematic and a relationship between a thickness and a width of each of sections, a ratio of the thicknesses of the respective sections, and the like differ from actual ones, and sections which differ in dimensional relationship or ratio may also be included among the drawings. Illustration of some of the components and assignment of reference numerals may be omitted.

An operation section 91 provided with various types of buttons configured to operate the endoscope 9 is disposed on a proximal end side of the insertion section 90 in the endoscope 9. The operation section 91 has a treatment instrument insertion opening of a channel 94 (see FIG. 2) into which living body forceps, an electrocautery, an inspection probe, and the like into the body cavity of the subject are inserted.

The insertion section 90 includes a rigid distal end section 90A in which an image pickup module 1 including an E/O-type optical module 3 (see FIG. 3) is disposed, a bendable bending section 90B consecutively connected to a proximal end side of the rigid distal end section 90A, and a flexible section 90C consecutively connected to a proximal end side of the bending section 90B. The bending section 90B is bent by an operation of the operation section 91.

A universal code 92 extending from the operation section 91 is connected to the processor 80 and the light source device 81 via a connector 93. A signal cable 40M configured to transmit an electric signal to be outputted by an O/E-type optical module 3X is inserted through the universal code 92.

The processor 80 controls the entire endoscope system 8 while performing signal processing for an image pickup signal to be outputted by the image pickup module 1 and outputting the image pickup signal as an image signal. The monitor 82 displays the image signal to be outputted by the processor 80.

The light source device 81 includes a white LED, for example. Illumination light to be emitted by the light source device 81 is guided to an illumination optical system 96 (see FIG. 2) in the rigid distal end section 90A via a light guide (not illustrated) that is inserted through the universal code 92 and the insertion section 90, to illuminate an object.

In other words, in the endoscope 9, an image pickup signal is converted into an optical signal by an optical module 3 in the rigid distal end section 90A, and is transmitted to the operation section 91 via a thin optical fiber 40 that is inserted through the insertion section 90. The optical signal is converted again into an electric signal by the O/E-type optical module 3X disposed in the operation section 91, and is transmitted to an electrical connector 93 via a signal cable 40M as a metal wiring that is inserted through the universal code 92. In other words, the image pickup signal is transmitted via the optical fiber 40 within the insertion section 90 having a small diameter, and is transmitted via the signal cable 40M as a thicker metal wiring than the optical fiber 40 within the universal code 92 which is not inserted into a body and an outer diameter of which is less restricted.

Note that if the optical module 3X is arranged in the connector 93 or the processor 80, the optical fiber 40 is inserted through the universal code 92.

Figure 2:
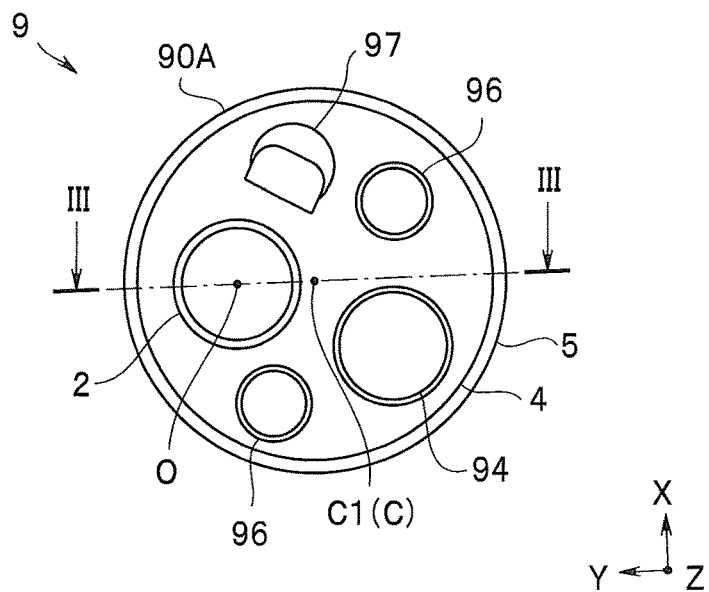
FIG. 2 is a plan view of a distal end section in the endoscope according to the first embodiment.

FIG. 2 is a front view of the rigid distal end section 90A in the endoscope 9 as viewed from a distal end side. The rigid distal end section 90A includes a cylindrical housing 4, which is tubular in its rear, an outer peripheral surface of which is covered with an outer skin 5 composed of a resin. The housing 4 has a plurality of through holes parallel to a distal end section central axis C1 as a central axis of the rigid distal end section 90A.

An observation window of an image pickup optical system 2 and an opening of the channel 94 are disposed on a distal end surface such that the distal end section central axis C1 (a central axis C of the insertion section 90) is interposed between the observation window and the opening. In other words, an optical axis O of the image pickup optical system 2 inserted into the through hole of the housing 4 is parallel to the distal end section central axis C1 (C) and is eccentric.

Illumination windows of two illumination optical systems 96 and a nozzle 97 for air feeding/water feeding are further disposed on the distal end surface.

Figure 3:
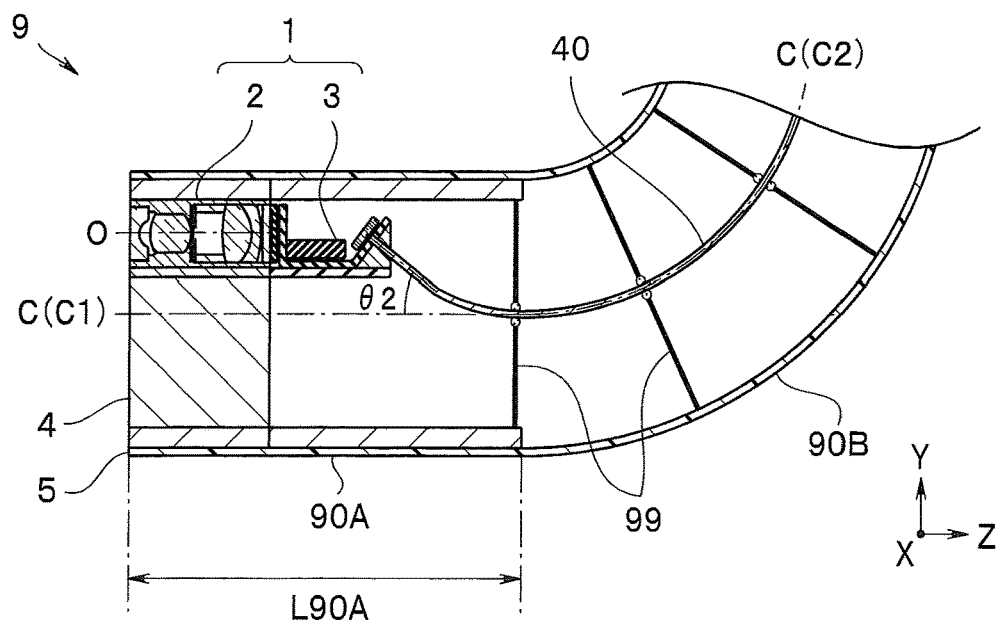
FIG. 3 is a cross-sectional view along a line III-III illustrated in FIG. 2 of the distal end section in the endoscope according to the first embodiment.

FIG. 3 illustrates a plane (YZ plane) including the optical axis O of the image pickup optical system 2 and the central axis C of the rigid distal end section 90A, as indicated by a line III-III illustrated in FIG. 2.

The image pickup module 1 including the image pickup optical system 2 and the optical module 3 is housed in the through hole of the housing 4 in the rigid distal end section 90A having a length L90A.

The optical fiber 40 extending from the image pickup module 1 includes a core having a diameter of 50 μm configured to transmit light and a clad having a diameter of 125 μm which covers an outer periphery of the core, for example. The optical fiber 40 a fiber distal end portion of which is inserted into the optical module 3 extends toward the distal end section central axis C1, and is arranged in the bending section 90B along a bending section central axis C2 of the bending section 90B.

In other words, guide members 99 configured to arrange the optical fiber 40 along the distal end section central axis C1 (the central axis C) are disposed in a proximal end portion of the distal end section 90A and the bending section 90B. Details of the guide member 99 are disclosed in Japanese Patent Application Laid-Open No. 2015-97589 already described. The guide members 99 are also preferably disposed in the flexible section 90C, although not illustrated. Note that the flexible section 90C is not more greatly deformed than the bending section 90B. Therefore, an arrangement spacing between the guide members 99 in the flexible section 90C may be longer than an arrangement spacing in the bending section 90B.

One multi-lumen tube having substantially the same outer diameter as an inner diameter of the bending section 90B and inserted through the bending section 90B may be used as the guide member. In other words, when the optical fiber 40 is inserted through a conduit that is in turn inserted through a center of the multi-lumen tube, the optical fiber 40 can be arranged along the central axis C.

To the optical fiber 40 inserted through the insertion section 90 in the endoscope 9, a stress is applied when the insertion section 90 is deformed. The optical fiber 40 receives a large stress particularly when the optical fiber 40 is deformed by a bending operation of the bending section 90B.

In the endoscope 9, the optical fiber 40 is arranged along the bending section central axis C2. Therefore, even if the bending section 90B is deformed, the optical fiber 40 does not receive a great stress. Accordingly, the endoscope 9 is high in reliability because the optical fiber 40 may not be damaged.

Further, as illustrated in FIG. 3, in the image pickup module 1 in the endoscope 9, the optical fiber 40 is arranged such that the fiber distal end portion is inclined by 45°±10°, i.e., not less than 35 degrees nor more than 55 degrees as a second angle $\theta 2$ to the distal end section central axis C1 in a cross section (YZ plane) including the central axis C and the optical axis O and to extend in a direction toward the distal end section central axis C1.

In an endoscope in which a fiber distal end portion of an optical fiber inserted into a ferrule is arranged parallel to the optical fiber, an optical axis of an optical element does not match the central axis of the rigid distal end section. Therefore, if the optical fiber is not greatly bent, the optical fiber cannot be arranged in a central axis of the bending section. "Greatly bend" means decreasing a radius of curvature (i.e., increasing a curvature). However, the optical fiber may be damaged when greatly bent. On the other hand, when a bending angle is reduced such that the optical fiber is not damaged, the rigid distal end section increases in length so that the endoscope 9 is not easily made minimally invasive.

On the other hand, in the endoscope 9, the optical fiber 40 can be arranged along the bending section central axis C2 without being greatly bent, as described above. Therefore, the endoscope 9 is high in reliability. Further, the optical fiber 40 can be arranged along the bending section central axis C2 in a short distance. Therefore, the endoscope 9 is minimally invasive because the length L90A of the distal end section 90A is small.

Figure 4:
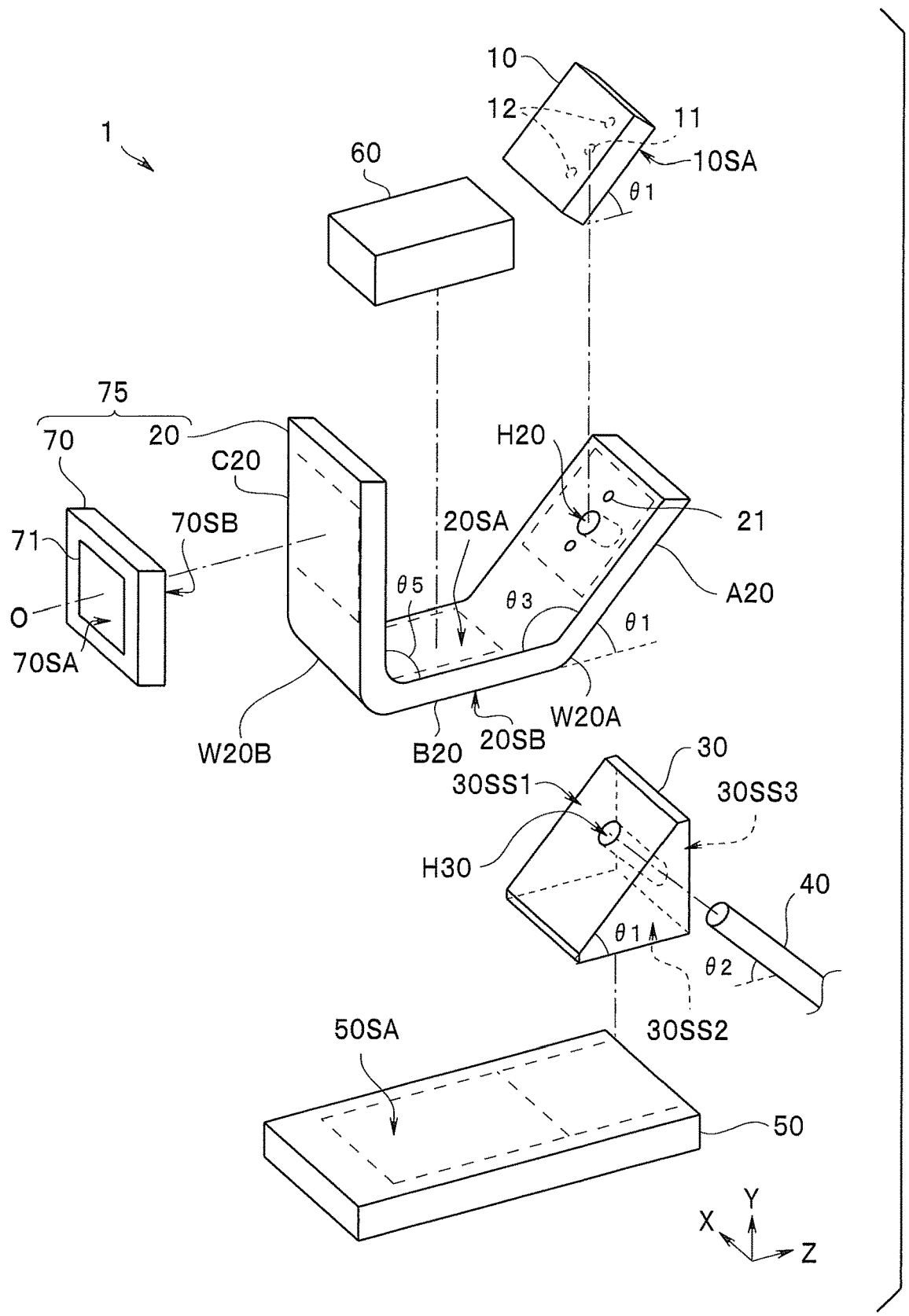
FIG. 4 is an exploded view of an image pickup module in the endoscope according to the first embodiment.

Details of the image pickup module 1 in the endoscope 9 will be described below with reference to FIGS. 4, 5A, and 5B.

The image pickup module 1 includes the image pickup optical system 2 and the optical module 3. An optical fiber 40 extends from the optical module 3.

In the image pickup optical system 2, a plurality of lenses 2A and an optical diaphragm 2B, for example, are housed in a lens barrel 2C. The optical module 3 includes a light emitting element 10, a wiring board 20, a ferrule 30 as a holding member, a substrate 50, a semiconductor chip component 60, and an image pickup device 70.

The wiring board 20 includes a first main surface 20SA and a second main surface 20SB. The wiring board 20 having flexibility includes a first region A20, a second region B20, and a third region C20. The first region A20 and the second region B20 are consecutively connected to each other via a first bent section W20A. The second region B20 and the third region C20 are consecutively connected to each other via a second bent section W20B.

Note that the first region A20, the first bent section W20A, the second region B20, the second bent section W20A, and the third region C20 are composed of one wiring board 20 having flexibility, and boundaries between them are not clear.

The substrate 50 is an inflexible flat plate composed of ceramic, glass, silicon, or the like. As long as a third main surface 50SA in the substrate 50 is planar, the substrate 50 is not limited to a parallel flat plate a main surface opposing the third main surface 50SA of which is parallel to the third main surface 50SA. A signal cable or the like may be connected to the substrate 50 on which a wiring and an electrode are disposed.

The wiring board 20, the substrate 50, and the ferrule 30 are bonded to one another with a bonding layer (not illustrated) interposed therebetween. Note that the substrate 50 and the ferrule 30 may be so-called three-dimensional substrates configured in one integral form using the same material.

The third main surface 50SA in the substrate 50 is arranged parallel to a wall surface of a through hole, parallel to the distal end section central axis C1, of the housing 4. Therefore, the second region B20 bonded to the third main surface 50SA is arranged parallel to the distal end section central axis C1. In other words, an angle of the second region B20 to the distal end section central axis C1 is zero degree.

On the other hand, the first region A20 is inclined at a third angle $\theta 3$ to the second region B20. In other words, the third angle $\theta 3$ as a bending angle of the first bent section W20A is not less than 125 degrees nor more than 145 degrees (135°±10°). The third angle $\theta 3$ is a supplementary angle of a first angle $\theta 1$ (see FIG. 4) of the ferrule 30 ($\theta 1+\theta 3=180°$).

Note that the third region C20 is perpendicular to the second region B20. In other words, a fifth angle $\theta 5$ as a bending angle of the second bent section W20B is 90 degrees.

A base of the wiring board 20 is flexible polyimide resin, for example. Note that in the wiring board, the first region A20 to the third region C20 may be respectively a rigid section having inflexibility, and the first bent section W20A and the second bent section W20B may be respectively a rigid flexible substrate having flexibility.

The light emitting element 10 is a surface emitting laser chip including a light emitting section 11 configured to output light of an optical signal. For example, a micro light emitting element 10 having planar-view dimensions of 250 μm×300 μm includes a light emitting section 11 having a diameter of 20 μm and an electrode 12 configured to feed a driving signal to the light emitting section 11 on a light emission surface 10SA.

Examples of the image pickup device 70 include a CMOS (complementary metal oxide semiconductor) image sensor and a CCD (charge coupled device). A light receiving section 71 is formed on a light receiving surface 70SA in the image pickup device 70, and an electrode 72 connected to the light receiving section 71 is disposed on a rear surface 70SB opposing the light receiving surface 70SA.

The semiconductor chip component 60 is a driving IC for driving the light emitting element 10. Note that not only the semiconductor chip component 60 but also a plurality of chip components such as a chip capacitor may be mounted on the wiring board 20, although not illustrated. Contrary to this, the semiconductor chip component 60 may not be mounted on the wiring board 20. Note that in the present specification, "disposition" means being fixed via an adhesive, for example, and "mounting" means being disposed on a surface and being electrically connected.

Power or the like is supplied to the semiconductor chip component 60 and the image pickup device 70, for example, via a cable not illustrated connected to the wiring board 20.

The first region A20 in the wiring board 20 includes a hole H20 as an optical path. The light emitting element 10 is flip-chip mounted on the first main surface 20SA in the first region A20 with the light emitting section 11 arranged at a position opposing the hole H20 in the wiring board 20. In other words, the wiring board 20 includes a plurality of electrodes 12 in the light emitting element 10 and electrode pads 21 to which the plurality of electrodes 12 are respectively bonded. Note that if the wiring board 20 includes a base that transmits light of an optical signal, the hole H20 as an optical path is not required.

The light emission surface 10SA is disposed parallel to the first region A20 in the wiring board 20. Accordingly, the light emission surface 10SA is inclined at a first angle θ1 of not less than 35 degrees nor more than 55 degrees to the distal end section central axis C1.

On the other hand, the ferrule 30 including an insertion hole H30 into which the fiber distal end portion of the optical fiber 40 is inserted is bonded to the second main surface 20SB in the first region A20.

An inner wall shape of the insertion hole H30 may be prismatic in addition to being columnar if the optical fiber 40 can be held on a wall surface of the insertion hole H30. Examples of a material for the ferrule 30 include glass, a metal member such as SUS, ceramic, or silicon.

The ferrule 30 in the image pickup module 1 is a substantially triangular prism including a first side surface 30SS1, a second side surface 30SS2, and a third side surface 30SS3. The insertion hole H30 has openings, each on the first side surface 30SS1 and the third side surface 30SS3.

The insertion hole H30 is perpendicular to the first side surface 30SS1, and an angle formed between the first side surface 30SS1 and the second side surface 30SS2 is the first angle θ1.

The wiring board 20 is a wiring member on which the image pickup device 70 is mounted, and the image pickup device 70 and the wiring member (the wiring board 20) constitute an image pickup unit 75. The light emitting element 10 is also mounted on the wiring board 20. As already described, the ferrule 30 is disposed on the wiring board 20 such that the insertion hole H30 faces the light emitting section 11 in the light emitting element 10 and the optical fiber 40 inserted into the insertion hole H30 is optically coupled to the light emitting element 10.

In the image pickup module 1, the first side surface 30SS1 in the ferrule 30 as a substantially triangular prism comes into surface contact with the second main surface in the first region A20 in the wiring board 20, and the second side surface 30SS2 comes into surface contact with the third main surface 50SA in the substrate 50. Therefore, an angle of the first bent section W20A can be easily and reliably made the third angle θ3.

When the optical fiber 40 is inserted into the insertion hole H30, the light emitting section 11 in the light emitting element 10 and the optical fiber 40 are automatically positioned.

Figure 5A:
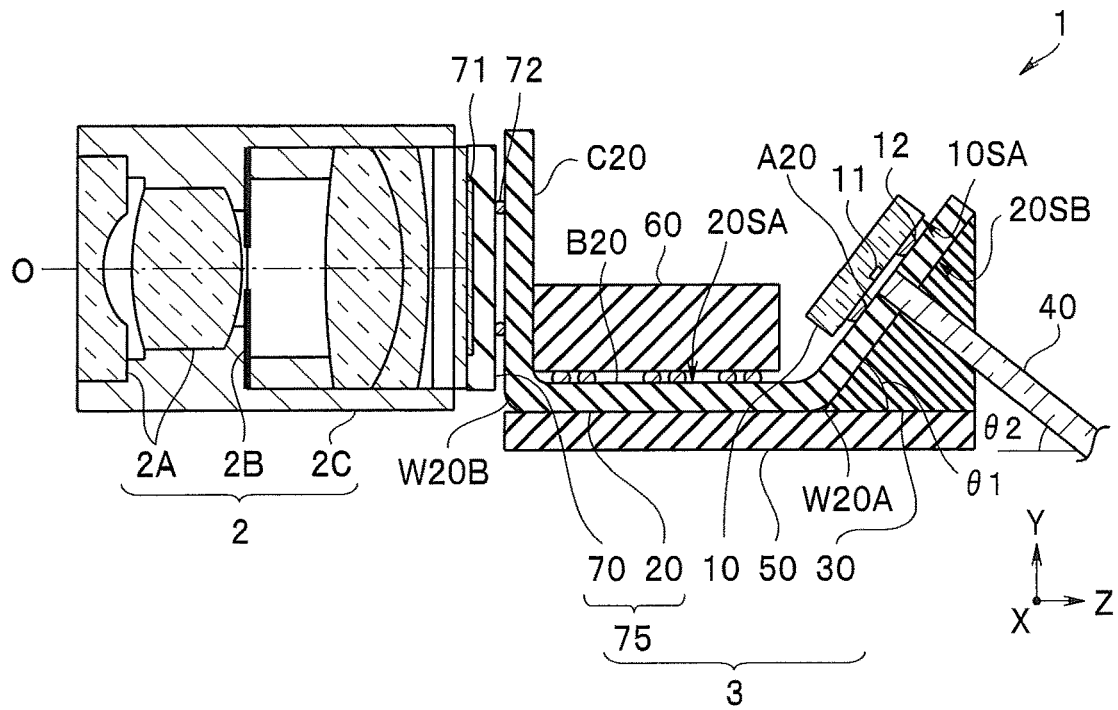
FIG. 5A is a cross-sectional view of the image pickup module in the endoscope according to the first embodiment.
Figure 5B:
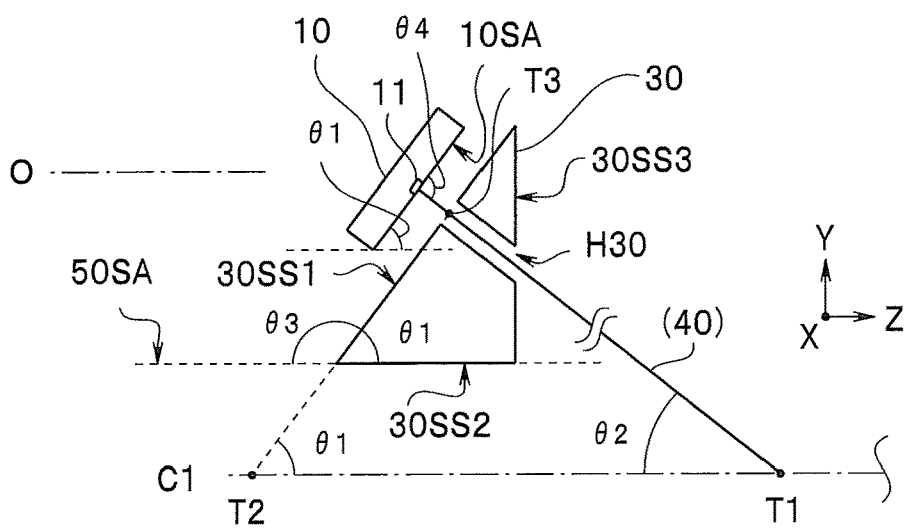
FIG. 5B is a cross-sectional view illustrating respective relative positions of components constituting an optical module in the endoscope according to the first embodiment.

FIG. 5A is a partially enlarged view of FIG. 3, and is a cross-sectional view illustrating a cut plane (YZ plane) including the optical axis O of the image pickup optical system 2 and the distal end section central axis C1. The optical axis O of the image pickup optical system 2 and the distal end section central axis C1 are parallel to each other. The third main surface 50SA is parallel to the optical axis O and the distal end section central axis C1. Strictly speaking, a line of intersection of the third main surface 50SA with a surface including the optical axis O and the distal end section central axis C1 is parallel to the optical axis O and the distal end section central axis C1. The second side surface 30SS2 in the ferrule 30 bonded to the third main surface 50SA is parallel to the optical axis O and the distal end section central axis C1.

On the other hand, the light emission surface 10SA in the light emitting element 10 and the first side surface 30SS1 in the ferrule are parallel to each other. A fourth angle θ (see FIG. 5B) to the insertion hole H30 in the ferrule 30, i.e., the light emission surface 10SA in the fiber distal end portion of the optical fiber 40 is 90 degrees. Accordingly, a coupling efficiency between the light emitting element 10 and the optical fiber 40 is high.

An angle of the light emission surface 10SA in the light emitting element 10 to the optical axis O (the distal end section central axis C1) is the same as the first angle θ1 formed between the first side surface 30SS1 and the second side surface 30SS2 in the ferrule 30. Since a total of interior angles of a triangle having T1, T2, and T3 as vertices is 180 degrees, the second angle θ2 of the optical fiber 40 to the distal end section central axis C1 is a complementary angle of the first angle θ1. In other words, an angle obtained by adding the first angle θ1 and the second angle θ2 is 90 degrees.

Since the first angle θ1 is not less than 35 degrees nor more than 55 degrees, the second angle θ2 is not less than 35 degrees nor more than 55 degrees.

Note that the image pickup device 70 is mounted on the second main surface 20SB in the third region C20 in the wiring board 20. The third region C20 abuts on a side surface of the semiconductor chip component 60 as a substantially rectangular parallelepiped mounted on the wiring board 20, to define an angle of the second bent section W20B, i.e., the fifth angle θ5 to the optical axis O (the distal end section central axis C1).

Note that the endoscope 9 may include an L-shaped member, for example, to define the fifth angle θ5 of the second bent section W20B.

As described above, in the endoscope 9, the light emission surface 10SA in the light emitting element 10 is inclined at the first angle θ1 to the central axis, and the fiber distal end portion of the optical fiber 40 is inclined at the second angle θ2 to the central axis. The first angle θ1 is a complementary angle of the second angle θ2. Therefore, the fourth angle θ4 of the fiber distal end portion of the optical fiber 40 to the light emission surface 10SA is 90 degrees. Accordingly, a coupling efficiency between the light emitting element 10 and the optical fiber 40 is high.

Further, the first angle θ1 and the second angle θ2 are defined to not less than 35 degrees nor more than 55 degrees by the ferrule 30. Accordingly, in the endoscope 9, the optical fiber 40 can be arranged along the bending section central axis C2 in a short distance. Therefore, the endoscope 9 is minimally invasive because the length L90A of the distal end section 90A is small.

Modification to First Embodiment

Image pickup modules in endoscopes 9A to 9B according to modifications to the first embodiment are similar to the image pickup module 1 in the endoscope 9, and hence components having the same functions are assigned the same reference numerals, to omit description of the components.

Modification 1 to First Embodiment

Figure 6:
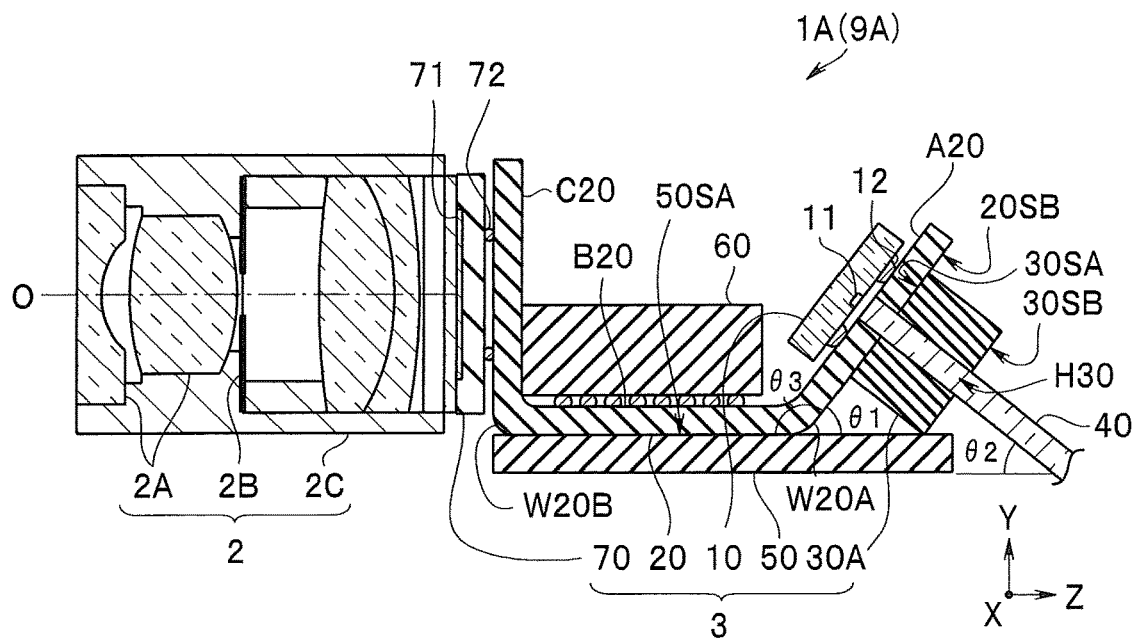
FIG. 6 is a cross-sectional view of an image pickup module in an endoscope according to Modification 1 to the first embodiment.

As illustrated in FIG. 6, a ferrule 30A in the image pickup module 1A in the endoscope 9A according to Modification 1 to the first embodiment is cylindrical in shape. An insertion hole H30 having openings, each on an upper surface 30SA and a lower surface 30SB is perpendicular to the upper surface 30SA and the lower surface 30SB.

The upper surface 30SA in the ferrule 30A is bonded to a second main surface 20SB in a first region A20 in a wiring board 20. On the other hand, a part of an outer periphery of the lower surface 30SB in the ferrule 30A abuts on a third main surface 50SA in a substrate 50.

When the ferrule 30A abuts on the third main surface 50SA in the substrate 50, a third angle θ3 of the first region A20 to a second region B20 in the wiring board 20 is defined. The third angle θ3 is a complementary angle of a first angle θ1 of a light emission surface 10SA in a light emitting element 10 to an optical axis O (a distal end section central axis C1). Further, the first angle θ1 is a complementary angle of a second angle θ2 of a fiber distal end portion of an optical fiber 40 to the optical axis O (the distal end section central axis C1).

Accordingly, in the image pickup module 1A, the first angle θ1 and the second angle θ2 are defined to 45°±10° by a length of the ferrule 30A.

If the first angle θ1 and the second angle θ2 are defined by the ferrule, a shape of the ferrule is not limited to a triangular prism or a cylinder, but may be a polygonal column or the like.

The endoscope 9A has the same effect as the effect of the endoscope 9.

Modification 2 to First Embodiment

Figure 7:
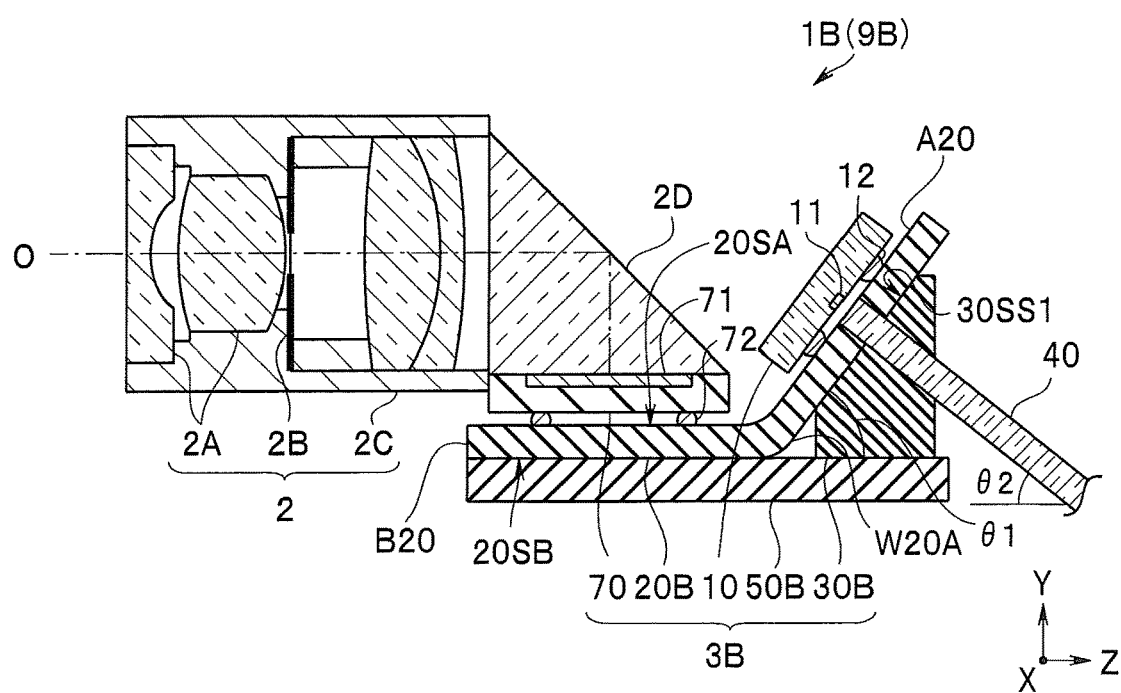
FIG. 7 is a cross-sectional view of an image pickup module in an endoscope according to Modification 2 to the first embodiment.

As illustrated in FIG. 7, a wiring board 20B in the image pickup module 1B in the endoscope 9B according to Modification 2 to the first embodiment includes a first region A20 and a second region B20, and does not include a third region.

The image pickup module 1B includes a right angle prism 2D configured to reflect light of an object image collected by an image pickup optical system 2. By the right angle prism 2D, an optical path of an optical signal is in a direction (Y-direction) perpendicular to an optical axis direction (Z-direction).

In other words, in the image pickup module 1B, an image pickup device 70 configured to receive light of the object image reflected by the right angle prism 2D is mounted on a first main surface 20SA in the second region B20 in the wiring board 20B.

The image pickup module 1B has the same effect as the effect of the image pickup module 1. Further, the wiring board 20B does not include a second bent section having a large bending angle. Therefore, a wiring may not be cut.

Note that a ferrule 30B may be a cylinder or the like, like in the image pickup module 1A, although a substantially triangular prism a corner of which is greatly chamfered.

Second Embodiment

An image pickup module 1C in an endoscope 9C according to a second embodiment is similar to the image pickup module 1 in the endoscope 9, for example, and hence components having the same functions are assigned the same reference numerals, to omit description of the components.

Figure 8:
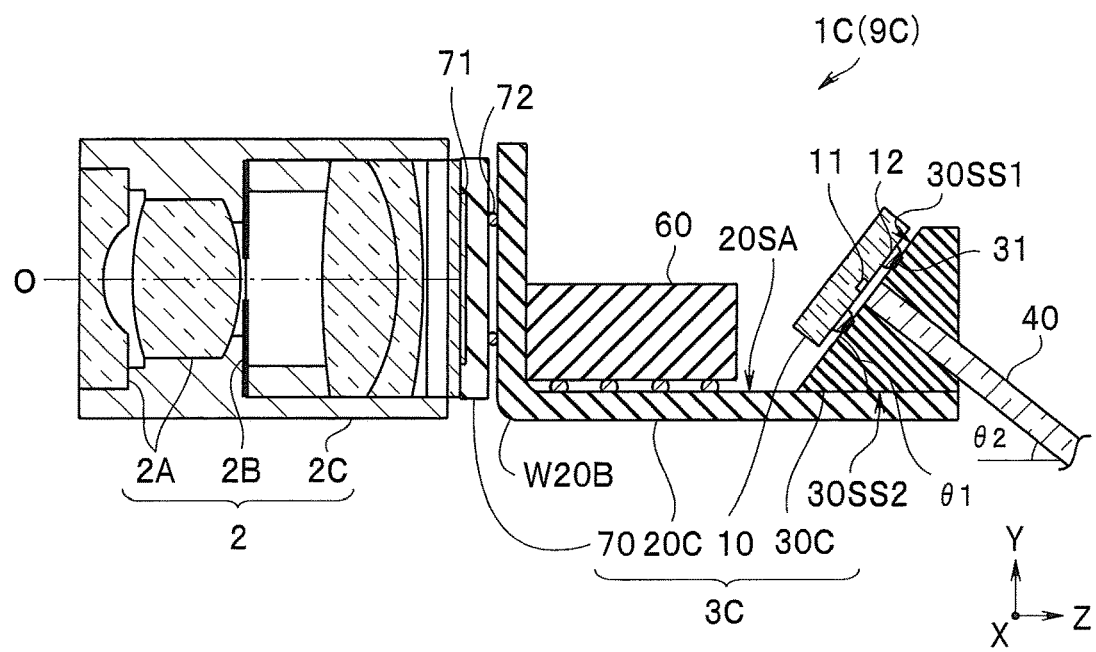
FIG. 8 is a cross-sectional view of an image pickup module in an endoscope according to a second embodiment.

As illustrated in FIG. 8, the image pickup module 1C does not include a substrate 50 as an inflexible flat plate, unlike the image pickup modules 1, 1A, and 1B.

A ferrule 30C as a substantially triangular prism is a three-dimensional wiring board composed of a molded circuit component (MID). An electrode pad 31 to which an electrode 12 in a light emitting element 10 is bonded is disposed on a first side surface 30SS1 in a ferrule 30C. On the other hand, a second side surface 30SS2 in the ferrule is bonded to a first main surface 20SA in a wiring board 20C. A wiring of the ferrule 30C is connected to a wiring of the wiring board 20C via a conductive paste or the like, although not illustrated.

The ferrule 30C is a molded circuit component (MID) including the electrode pad 31 and a wiring (not illustrated) using a non-conductive resin as a base material. The ferrule 30C may be a three-dimensional wiring board composed of ceramic.

The ferrule 30C in the image pickup module 1C has a function of a wiring board on which the light emitting element 10 is mounted simultaneously with defining a direction of a fiber distal end portion of an optical fiber 40 (a second angle θ2).

The endoscope 9C has the same effect as the effect of the endoscope 9.

Modification to Second Embodiment

Image pickup modules 1D and 1E in endoscopes 9D and 9E respectively according to modifications to the second embodiment are similar to the image pickup module 1B in the endoscope 9B and the image pickup module 1C in the endoscope 9C, and hence components having the same functions are assigned the same reference numerals, to omit description of the components.

Modification 1 to Second Embodiment

Figure 9:
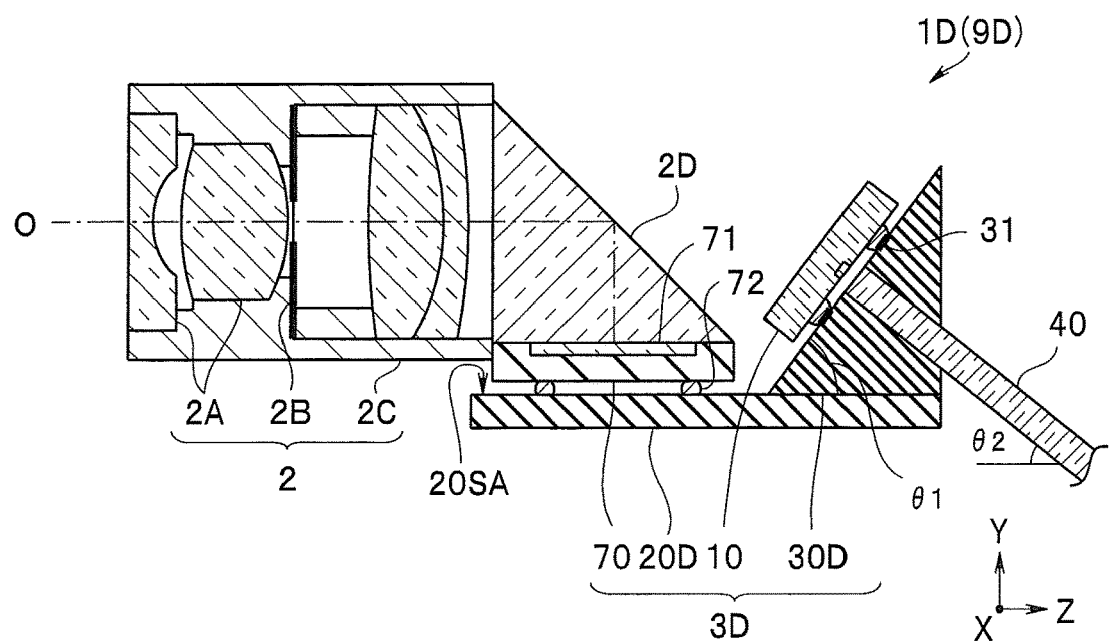
FIG. 9 is a cross-sectional view of an image pickup module in an endoscope according to Modification 1 to the second embodiment.

As illustrated in FIG. 9, a wiring board 20D in the image pickup module 1D in the endoscope 9D according to Modification 1 to the second embodiment has a shape of a flat plate including no bent section. Accordingly, the wiring board 20D may be inflexible. An image pickup device 70 configured to receive light of an object image reflected by a right angle prism 2D as a prism and a ferrule 30D as a three-dimensional wiring board composed of MID are disposed on a first main surface 20SA in the wiring board 20D.

The endoscope 9D has the respective effects of the endoscope 9B and the endoscope 9C. Further, the endoscope 9D is more easily manufactured because a configuration of the image pickup module 1D is simpler than the configuration of the image pickup module 1B, for example.

Modification 2 to Second Embodiment

Figure 10:
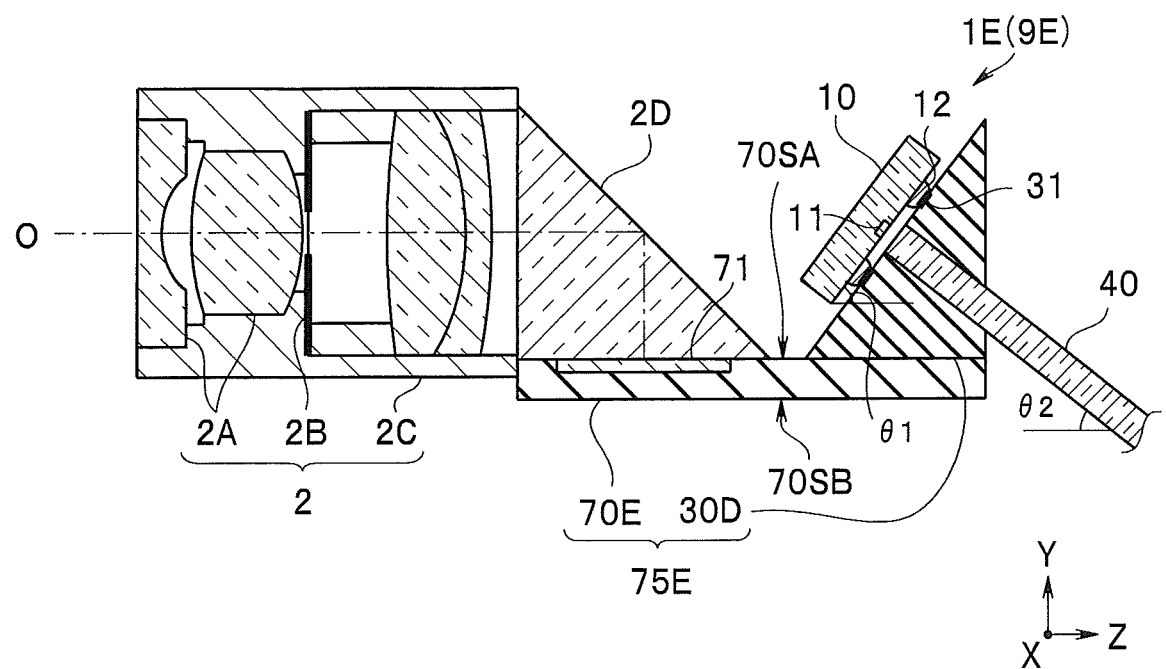
FIG. 10 is a cross-sectional view of an image pickup module in an endoscope according to Modification 2 to the second embodiment.

As illustrated in FIG. 10, in the image pickup module 1E in the endoscope 9E according to Modification 2 to the second embodiment, a right angle prism 2D as a prism and a ferrule 30D as a three-dimensional wiring board composed of MID are disposed on a light receiving surface 70SA in an image pickup device 70E. In other words, the image pickup module 1E does not include a wiring board 20D, although similar to the image pickup module 1D.

The image pickup device 70E having a function of the wiring board 20D and the ferrule 30D constitute an image pickup unit 75E. An electrode connected to the ferrule 30D as a three-dimensional wiring board is disposed on the light receiving surface 70SA, although not illustrated. An electronic component may be mounted on the image pickup device 70E.

The endoscope 9E has an effect of the endoscope 9D. Further, the endoscope 9E is more easily manufactured because a configuration of the image pickup module 1E is simpler than the configuration of the image pickup module 1D, for example.

Third Embodiment

An image pickup module 1F in an endoscope 9F according to a third embodiment is similar to the image pickup module 1 in the endoscope 9, for example, and hence components having the same functions are assigned the same reference numerals, to omit description of the components.

Figure 11:
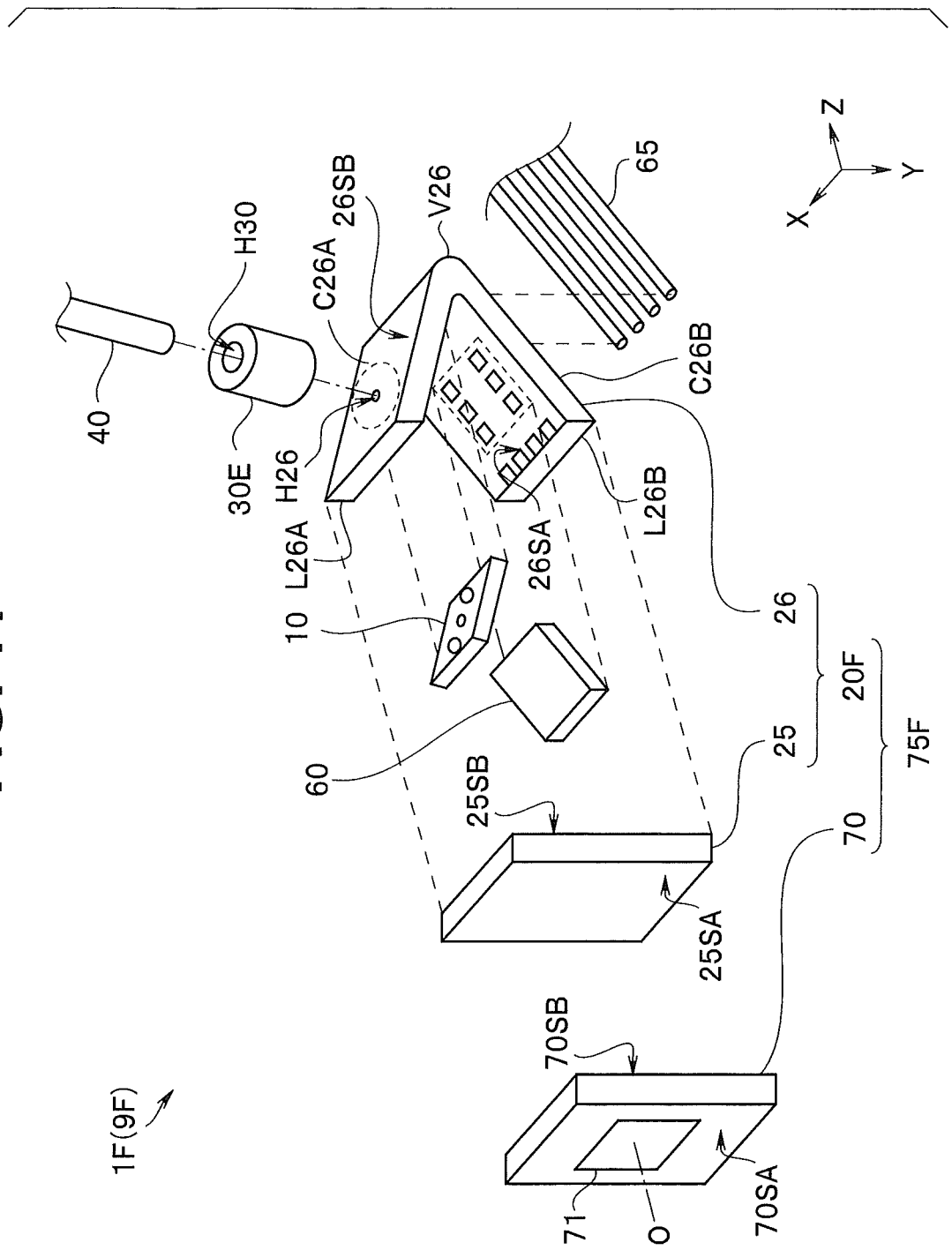
FIG. 11 is an exploded view of an image pickup module in an endoscope according to a third embodiment.
Figure 12A:
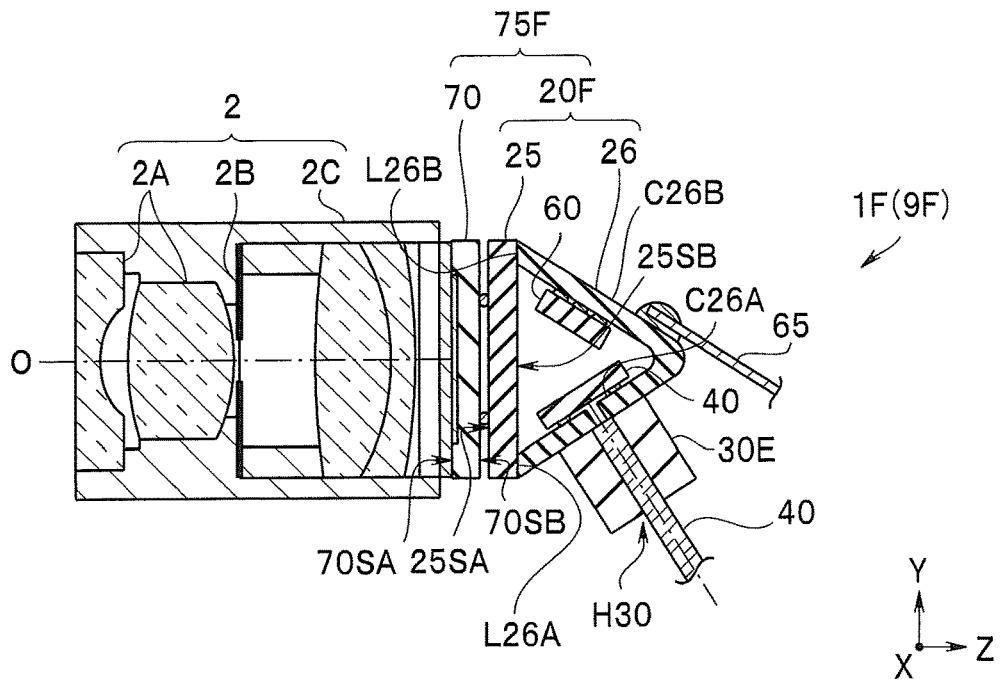
FIG. 12A is a cross-sectional view of an image pickup module in an endoscope according to Modification 2 to the third embodiment.

As illustrated in FIGS. 11 and 12A, in the image pickup module 1F, a wiring member 20F in an image pickup unit 75F includes a second wiring board 25 and a bent wiring board 26. On the other hand, a ferrule 30E has a shape of a cylinder including an insertion hole H30.

The second wiring board 25 includes a seventh main surface 25SA and an eighth main surface 25SB opposing the seventh main surface 25SA. A rear surface 70SB in an image pickup device 70 is mounted on the seventh main surface 25SA. The seventh main surface 25SA and the eighth main surface 25SB in the second wiring board 25 are parallel surfaces parallel to a light receiving surface 70SA in the image pickup device 70.

The bent wiring board 26 includes a fifth main surface 26SA as an inner surface and a sixth main surface 26SB as an outer surface opposing the fifth main surface 26SA. The bent wiring board 26 in which a rectangular flat wiring board is bent by a bent section V26 has a substantially V shape when observed in a side surface direction (X-axis direction). The bent section V26 in the bent wiring board 26 is perpendicular to a long side of a rectangle, and is parallel to two sides L26A and L26B, and the two opposing sides L26A and L26B are arranged on the same plane.

A light emitting element 10 is mounted, out of two regions C26A and C26B on both sides of the bent section V26 in the bent wiring board 26, on the fifth main surface 26SA in the region C26A. On the other hand, the ferrule 30E is disposed on the sixth main surface 26SB in the region C26A such that the insertion hole H30 faces a light emitting section 11 in the light emitting element 10. A central axis of the insertion hole H30 in the ferrule 30E matches an optical axis of the light emitting element 10. Accordingly, an optical fiber 40 inserted into the insertion hole H30 is optically coupled to the light emitting element 10.

Note that the bent wiring board 26 is an inflexible substrate in which a bending angle of the bent section V26 is previously set to a predetermined angle. A chip component 60 such as a driving IC for the light emitting element 10 is mounted on the fifth main surface 26SA in the bent wiring board 26, and a cable 65 is bonded to the sixth main surface 26SB.

Figure 12B:
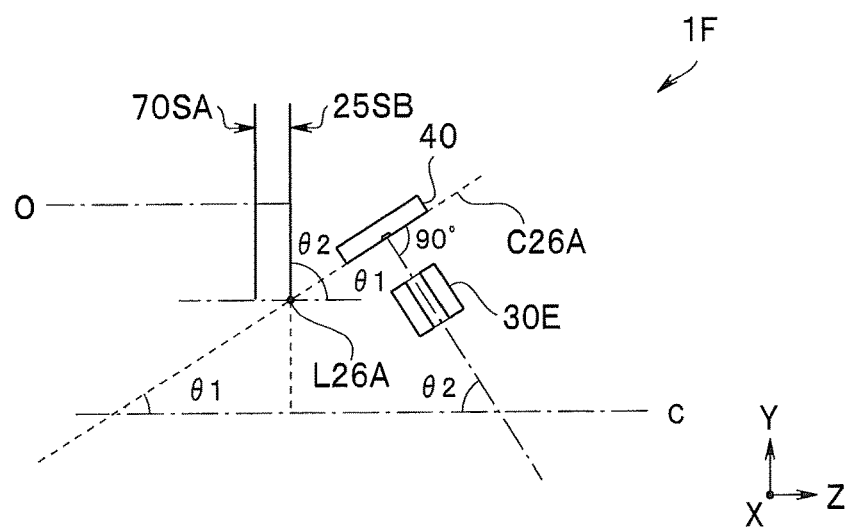
FIG. 12B is a cross-sectional view illustrating respective relative positions of components constituting an optical module in the endoscope according to the third embodiment.

As illustrated in FIG. 12B, when two opposing sides L26A and L26B in the bent wiring board 26 are arranged to abut on an eighth main surface 25SB in the second wiring board 25, an angle θ1 of the region C26A to the eighth main surface 25SB as a parallel surface parallel to the light receiving surface 70SA is defined. An angle of the central axis of the insertion hole H30 in the ferrule 30 to the eighth region C26A is 90 degrees. A second angle θ2 of the region C26A to a central axis C of a fiber distal end portion is defined because (θ1+θ2=90°).

In other words, in the image pickup module 1F, the second angle θ2 is defined by the bent wiring board 26 on which the ferrule 30E is disposed, and the optical fiber 40 is arranged to extend in a direction toward a distal end section central axis C1. The endoscope 9F is high in reliability because the optical fiber 40 can be arranged along a bending section central axis C2 without being greatly bent. Further, the optical fiber 40 can be arranged along the bending section central axis C2 in a short distance. Therefore, the endoscope 9F is minimally invasive because a length L90A of a rigid distal end section 90A is small.

Modifications to Third Embodiment

Image pickup modules 1G to 1J in endoscopes 9G to 9J are similar to the image pickup module 1F in the endoscope F, for example, and hence components having the same functions are assigned the same reference numerals, to omit description of the components.

Modification 1 to Third Embodiment

Figure 13:
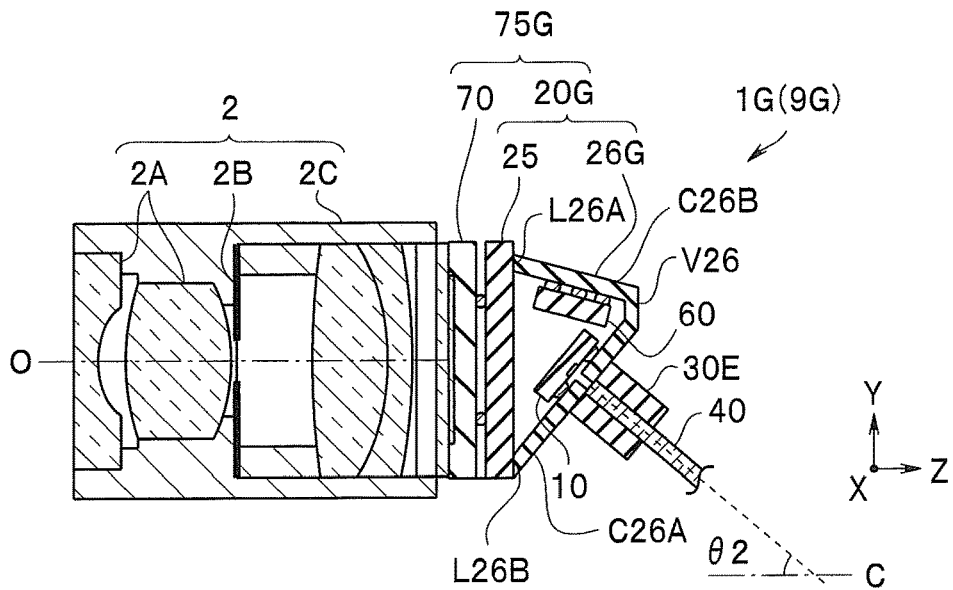
FIG. 13 is a cross-sectional view of an image pickup module in an endoscope according to Modification 1 to the third embodiment.

As illustrated in FIG. 13, in a bent wiring board 26G in the image pickup module 1G in the endoscope 9G according to Modification 1 to the third embodiment, respective sizes of regions C26A and C26B on both sides of a bent section V26 and angles to an eighth main surface 25SB as a parallel surface parallel to a light receiving surface 70SA differ from each other.

A second angle θ2 of a fiber distal end portion to a central axis C is (θ1+θ2=90°). Therefore, the second angle θ2 of the fiber distal end portion to the central axis C is defined by only an angle θ1 of the region C26A to the eighth main surface 25SB as a parallel surface parallel to the light receiving surface 70SA.

Modification 2 to Third Embodiment

Figure 14:
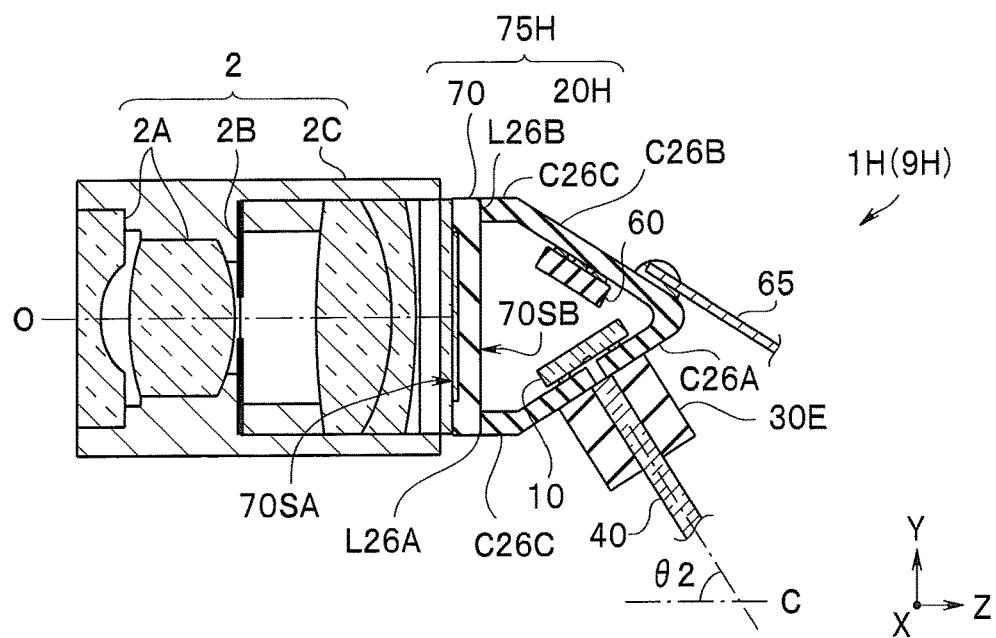
FIG. 14 is a cross-sectional view of an image pickup module in an endoscope according to Modification 2 to the third embodiment.

As illustrated in FIG. 14, in the image pickup module 1H in the endoscope 9H according to Modification 2 to the third embodiment, two opposing sides L26A and L26B of a bent wiring board 26H as a wiring member 20H abut on a rear surface 70SB in an image pickup device 70. It goes without saying that the rear surface 70SB is a parallel surface parallel to a light receiving surface 70SA.

The wiring member 20H includes extension sections C26C respectively extending from regions C26A and C26B. The extension section C26C is arranged perpendicularly to the rear surface 70SB (parallel surface) of the image pickup device 70. However, an angle θ1 of the region C26A on which a light emitting element 10 is mounted to the parallel surface is defined by the two opposing sides L26A and L26B abutting on the parallel surface.

In the image pickup module 1H, wirings are more easily connected to each other, for example, because the two sides L26A and L26B are arranged perpendicularly to the rear surface 70SB than in the image pickup module 1G.

Modification 3 to Third Embodiment

Figure 15:
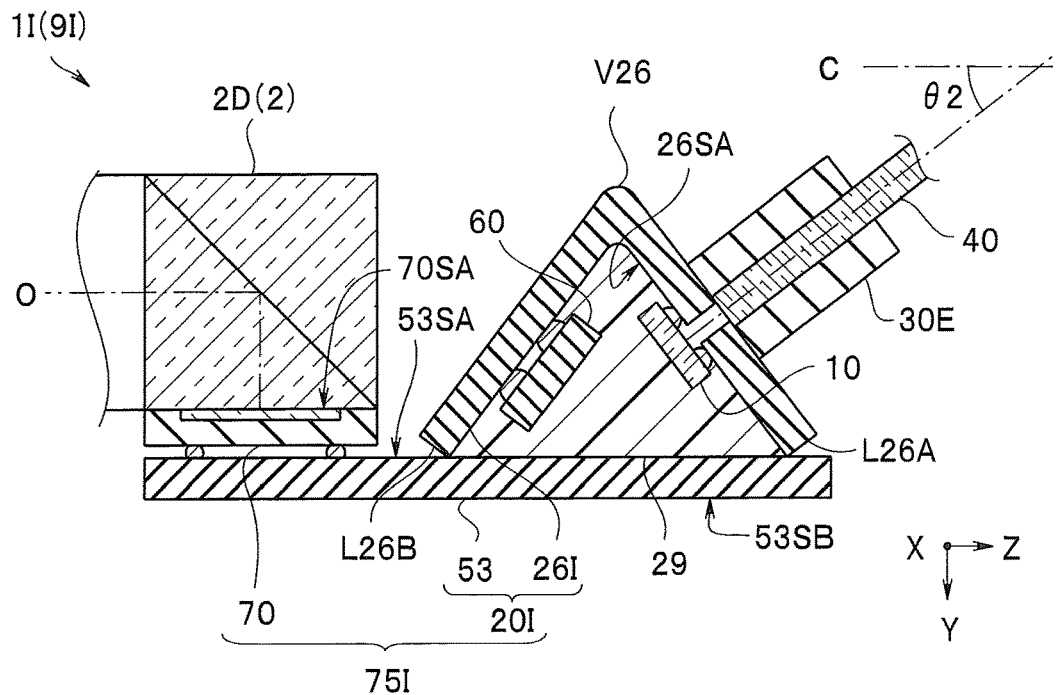
FIG. 15 is a cross-sectional view of an image pickup module in an endoscope according to Modification 3 to the third embodiment.

As illustrated in FIG. 15, the image pickup module 1I in the endoscope 9I according to Modification 3 to the third embodiment includes a right angle prism 2D, an image pickup device 70, a third wiring board 53, and a bent wiring board 26I. The third wiring board 53 and the bent wiring board 26I constitute a wiring member 20I on which the image pickup device 70 is mounted, and the image pickup device 70 and the wiring member 20I constitute an image pickup unit 75I.

The right angle prism 2D is a prism configured to reflect light of an object image collected by an image pickup optical system 2. The third wiring board 53 includes a ninth main surface 53SA and a tenth main surface 53SB opposing the ninth main surface 53SA.

The image pickup device 70 is mounted on the ninth main surface 53SA as a parallel surface, and two opposing sides L26A and L26B of the bent wiring board 26I abut on the ninth main surface 53SA. Although the bent wiring board 26I is a flexible wiring board, a resin 29 is subjected to curing treatment after an inner side of a bent section V26, that is, a space between the fifth main surface 26SA and the ninth main surface 53SA is filled with the resin 29. Therefore, a bending angle of the bent section V26 is defined to a predetermined angle.

The image pickup module 1I can define a second angle θ2 of a fiber distal end portion to a central axis C by performing filling/curing treatment of the resin 29 after finely adjusting a bending angle of the bent wiring board 26I.

Modification 4 to Third Embodiment

Figure 16:
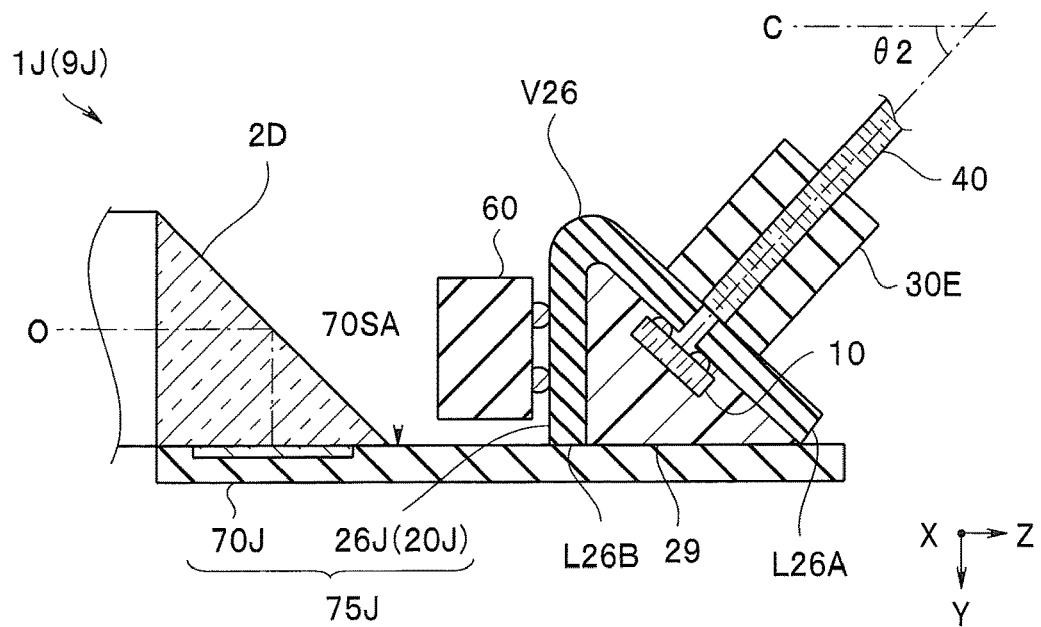
FIG. 16 is a cross-sectional view of an image pickup module in an endoscope according to Modification 4 to the third embodiment.

As illustrated in FIG. 16, in the image pickup module 1J in the endoscope 9J according to Modification 4 to the third embodiment, a right angle prism 2D is disposed on a light receiving surface 70SA in an image pickup device 70J. In other words, a bent wiring board 26J is a wiring member 20J, and an image pickup unit 75J includes the image pickup device 70J and the bent wiring board 26J.

When two opposing sides L26A and L26B of the bent wiring board 26J abut on the light receiving surface 70SA, a second angle θ2 of a fiber distal end portion to a central axis C can be defined.

The image pickup module 1J has an effect of the image pickup module 1I, and is further simply configured.

Fourth Embodiment

An image pickup module 1K in an endoscope 9K according to a fourth embodiment is similar to the image pickup module 1D in the endoscope 9D, for example, and hence components having the same functions are assigned the same reference numerals, to omit description of the components.

Figure 17:
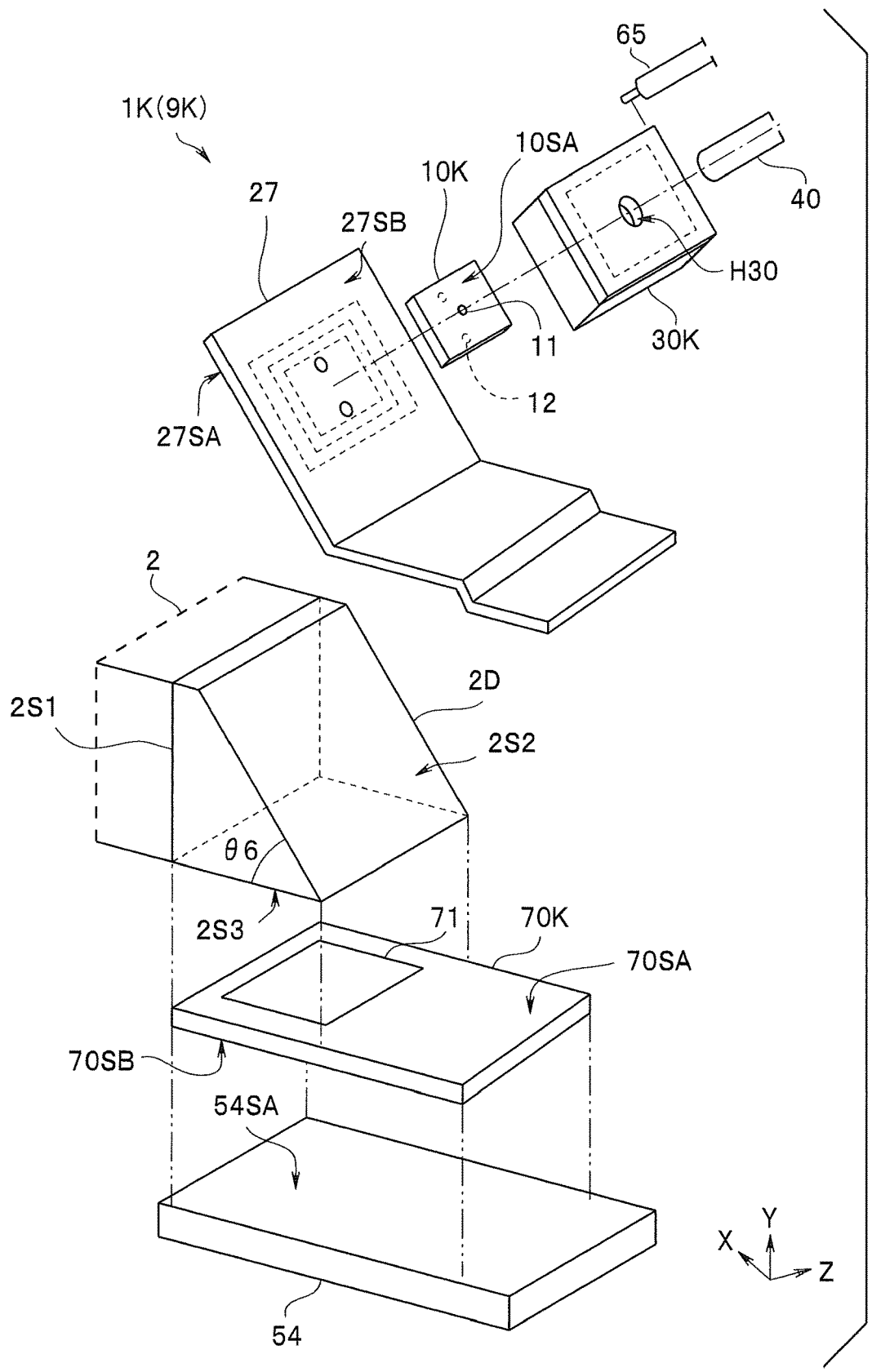
FIG. 17 is an exploded view of an image pickup module in an endoscope according to a fourth embodiment.
Figure 18A:
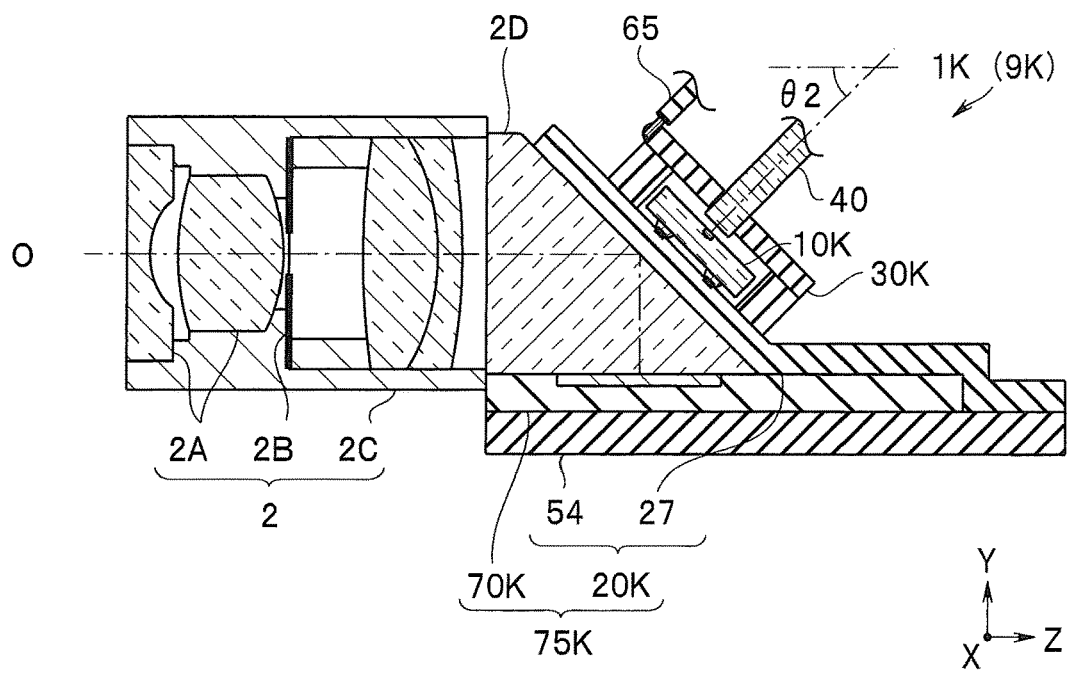
FIG. 18A is a cross-sectional view of the image pickup module in the endoscope according to the fourth embodiment.
Figure 18B:
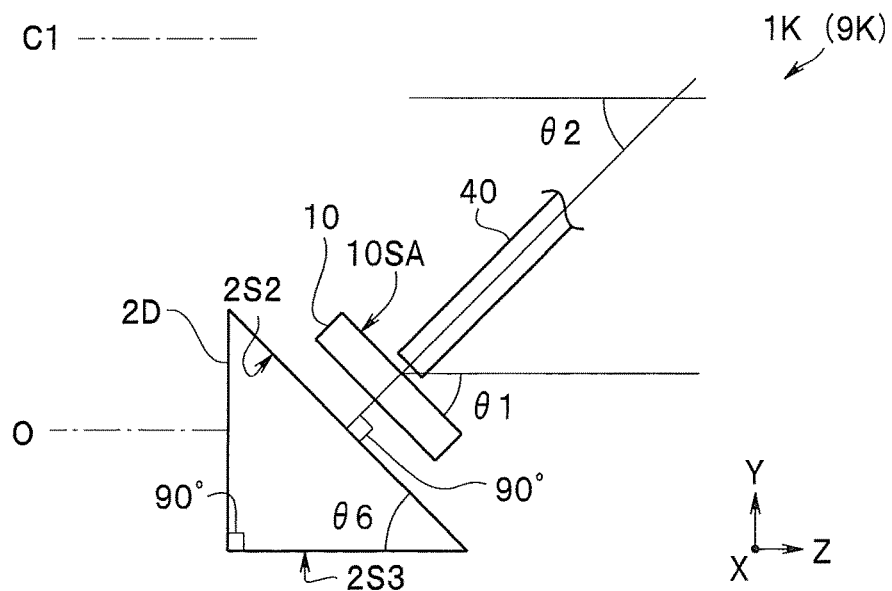
FIG. 18B is a cross-sectional view illustrating respective relative positions of components constituting an optical module in the endoscope according to the fourth embodiment.

The image pickup module 1K further includes a prism 2D, as illustrated in FIGS. 17, 18A, and 18B. The prism 2D includes an incidence surface 2S1 on which light of an object image collected by the image pickup optical system 2 is incident, a reflection surface 2S2 on which light of the object image is reflected, and an emission surface 2S3 from which light of the object image is emitted. Light of the object image collected by the image pickup optical system 2 is reflected on the reflection surface 2S2 and is incident on a light receiving section 71 in an image pickup device 70K.

A wiring member 20K in an image pickup unit 75K includes a fourth wiring board 27 including a tenth main surface 27SA and an eleventh main surface 27SB opposing the tenth main surface 27SA. A light emitting element 10K is mounted on the eleventh main surface 27SB in the fourth wiring board 27. In the light emitting element 10K, an electrode 12 connected to a light emitting section 11 is disposed on a rear surface opposing a light emission surface 10SA including the light emitting section 11.

The tenth main surface 27SA in the fourth wiring board 27 is disposed on the reflection surface 2S2 in the prism 2D and a light receiving surface 70SA in the image pickup device 70K. In other words, the fourth wiring board 27 having flexibility is folded.

As illustrated in FIG. 18B, in an image pickup module 1, a first angle θ1 and a second angle θ2 are defined by an inclination angle θ6 of the reflection surface 2S2 to the emission surface 2S3 in the prism 2D.

For example, if the prism 2D is a right angle prism, the inclination angle θ6 is 45 degrees. Accordingly, the first angle θ1 to a central axis of the light emission surface 10SA in the light emitting element 10K parallel to the inclined surface 2S2 is 45 degrees. Since an optical fiber 40 is arranged perpendicularly to the light emission surface 10SA, the second angle θ2 of a distal end portion of the optical fiber 40 to a distal end section central axis C1 is also 45 degrees.

The optical fiber 40 extends backward at the second angle θ2, and therefore can be arranged along a bending section central axis C2 in a short distance. Accordingly, the endoscope 9K is minimally invasive because a length L90A of a rigid distal end section 90A is small.

Note that the image pickup module 1K further includes a ferrule wiring board 30K and a substrate 54. The ferrule wiring board 30K includes a recessed portion in which the light emitting element 10K is housed and a through hole H30 into which the distal end portion of the optical fiber 40 is inserted. A cable 65 is bonded to the ferrule wiring board 30K. A rear surface 70SB in the image pickup device 70K is disposed on a main surface 54SA in the substrate 54. The substrate 54 is a reinforcing member for the image pickup device 70K, and is not an essential component for the image pickup module 1K.

In the image pickup module 1K, the light emitting element 10K is arranged in a space on the prism 2D which is an essential component and on which image pickup light is reflected. In other words, the light emitting element 10K is housed in a space formed by extending the incidence surface 2S1 in the prism 2D in an optical axis direction of the image pickup optical system 2. Accordingly, in the endoscope 9K, the rigid distal end section 90A is easily reduced in diameter.

Modification to Fourth Embodiment

An image pickup module 1L in an endoscope 9L according to a modification to the fourth embodiment is similar to the image pickup module 1K in the endoscope 9K, and hence components having the same functions are assigned the same reference numerals, to omit description of the components.

Figure 19:
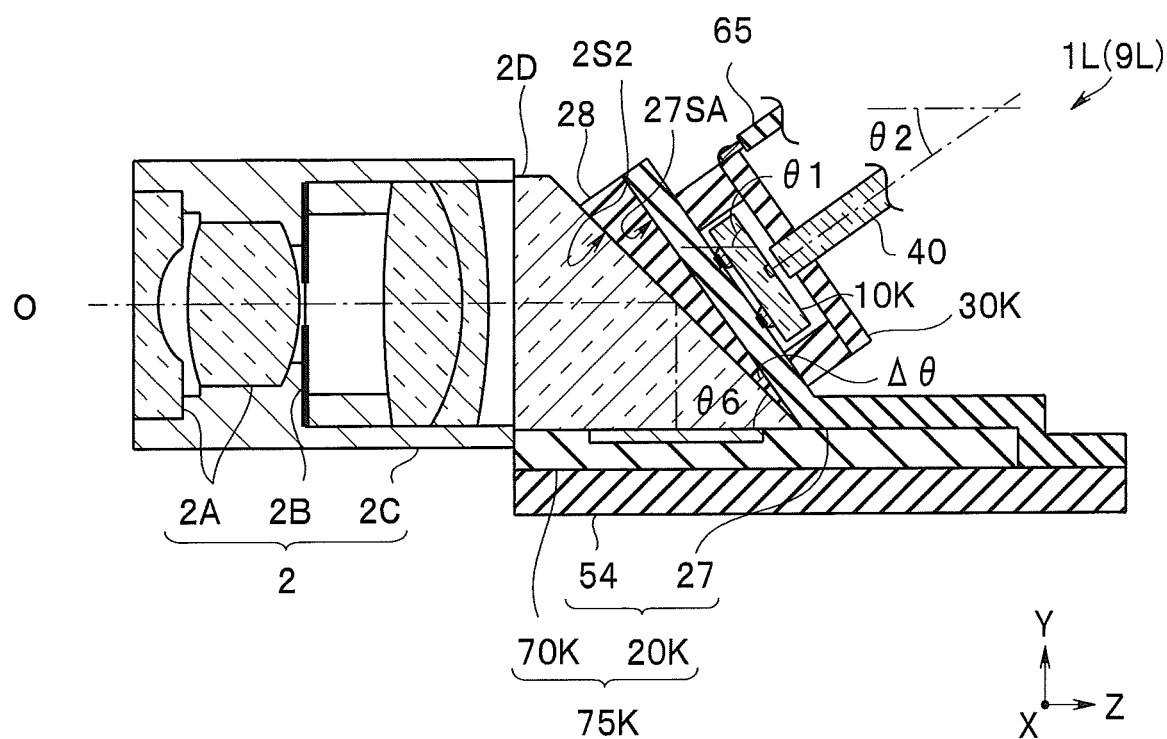
FIG. 19 is a cross-sectional view of an image pickup module in an endoscope according to Modification to the fourth embodiment.

As illustrated in FIG. 19, the image pickup module 1L further includes a spacer 28 disposed between a tenth main surface 27SA in a fourth wiring board 27 and a reflection surface 2S2 in a prism 2D.

As already described, in the image pickup module 1K, if the prism 2D is the right angle prism, the inclination angle $\theta 6$ is 45 degrees. Therefore, the first angle $\theta 1$ and the second angle $\theta 2$ are also 45 degrees. However, if the optical fiber 40 is not greatly bent when the second angle $\theta 2$ is 45 degrees, the optical fiber 40 may be unable to be arranged along the bending section central axis C2 depending on a specification of the endoscope.

In the image pickup module 1L, even if an inclination angle $\theta 6$ is 45 degrees, a first angle $\theta 1$ to a central axis C of a light emission surface 10SA in a light emitting element 10K is $(45+\Delta\theta°)$ by the spacer 28. Accordingly, the second angle $\theta 2$ is $(45-\Delta\theta°)$.

In other words, the first angle $\theta 1$ and the second angle $\theta 2$ can be adjusted by the spacer 28. The spacer 28 is not limited to a wedge-shaped spacer if an angle $\Delta\theta$ between the tenth main surface 27SA and the reflection surface 2S2 can be defined.

The present invention is not limited to the above-described embodiments and modifications, but various modifications, combinations, and applications are possible without departing from the scope and spirit of the invention.

What is claimed is:

1. An endoscope comprising an insertion section including a rigid distal end section, a bending section, and a flexible section consecutively connected to one another, an image pickup module configured to emit an optical signal being disposed in the rigid distal end section in the insertion section, wherein
   the image pickup module comprises:
   an image pickup optical system an optical axis of which is parallel to a distal end section central axis of the rigid distal end section and is eccentric from the distal end section central axis;
   an image pickup unit including an image pickup device including a light receiving surface for receiving light of an object image collected by the image pickup optical system and a rear surface;
   a light emitting element configured to convert an image pickup signal outputted by the image pickup device into the optical signal and emit the optical signal from a light emission surface;
   an optical fiber configured to transmit the optical signal; and
   a ferrule including an insertion hole and disposed in the image pickup unit at a position where the optical fiber inserted into the insertion hole is optically coupled to the light emitting element,
   the light emission surface in the light emitting element is inclined at a first angle of not less than 35 degrees nor more than 55 degrees to the distal end section central axis, and
   the optical fiber has a fiber distal end portion, which is inserted into the insertion hole in the ferrule, inclined at a second angle of not less than 35 degrees nor more than 55 degrees to the distal end section central axis, extends toward the distal end section central axis, and is arranged along a bending section central axis in the bending section.

2. The endoscope according to claim 1, wherein the image pickup unit includes a wiring member on which the image pickup device is mounted.

3. The endoscope according to claim 2, wherein the wiring member is a wiring board which includes a first main surface and a second main surface, the image pickup device being mounted on the first main surface, and the first angle and the second angle are defined by the ferrule disposed on the wiring board.

4. The endoscope according to claim 3, wherein the ferrule includes a first side surface, a second side surface, and a third side surface, the insertion hole including openings, each on the first side surface and the third side surface, and
an angle formed between the first side surface and the second side surface is the first angle.

5. The endoscope according to claim 4, wherein the image pickup module further comprises a substrate including a third main surface,
the wiring board includes a first region and a second region consecutively connected to each other via a first bent section,
the light emitting element is mounted on the first main surface in the first region,
the first side surface in the ferrule is bonded to the second main surface in the first region, and
the second main surface in the second region and the second side surface in the ferrule are bonded to the third main surface in the substrate.

6. The endoscope according to claim 5, wherein the wiring board includes a third region consecutively connected to the second region via a second bent section, and
the image pickup device is mounted on the second main surface in the third region in the wiring board, and the third region is perpendicular to the second region.

7. The endoscope according to claim 5, wherein the image pickup module further comprises a prism configured to reflect an object image collected by the image pickup optical system, and
the image pickup device configured to receive light of the object image reflected by the prism is mounted on the first main surface in the second region in the wiring board.

8. The endoscope according to claim 4, wherein the ferrule is a three-dimensional wiring board, and
the light emitting element is mounted on the first side surface, and the second side surface is bonded to the first main surface.

9. The endoscope according to claim 8, wherein the wiring board includes a second region and a third region consecutively connected to each other via a second bent section,
the ferrule is disposed in the second region, and
the image pickup device is mounted on the second main surface in the third region, and the third region is perpendicular to the second region.

10. The endoscope according to claim 3, wherein the image pickup module further comprises a prism configured to reflect an object image collected by the image pickup optical system, and
the image pickup device configured to receive light of the object image reflected by the prism is mounted on the first main surface.

11. The endoscope according to claim 1, wherein the image pickup module further comprises a reflection section configured to reflect an object image collected by the image pickup optical system, and
the reflection section and the ferrule that defines the first angle and the second angle are disposed on the light receiving surface in the image pickup device.

12. The endoscope according to claim 2, wherein
the wiring member comprises
a bent wiring board including a fifth main surface and a sixth main surface, the light emitting element being mounted on the fifth main surface, and the ferrule being disposed to face the light emitting element on the sixth main surface, and
the bent wiring board includes a bent section bent such that two opposing sides are arranged on a same plane, and the two opposing sides are arranged on a parallel surface parallel to the light receiving surface in the image pickup device to define the first angle and the second angle.

13. The endoscope according to claim 12, wherein
the wiring member further comprises
a second wiring board including a seventh main surface and an eighth main surface, the rear surface in the image pickup device being mounted on the seventh main surface,
the two opposing sides in the bent wiring board abutting on the eighth main surface as the parallel surface.

14. The endoscope according to claim 12, wherein
the two opposing sides in the bent wiring board abut on the rear surface in the image pickup device as the parallel surface.

15. The endoscope according to claim 12, wherein
the image pickup module further comprises a prism configured to reflec an object image collected by the image pickup optical system, and
the wiring member comprises
a third wiring board including a ninth main surface and a tenth main surface,
the image pickup device being mounted on the ninth main surface as the parallel surface, and the two opposing sides in the bent wiring board abutting on the ninth main surface.

16. The endoscope according to claim 12, wherein
the image pickup module further comprises a prism configured to reflect an object image collected by the image pickup optical system, and
the prism is disposed on the light receiving surface in the image pickup device, and the two opposing sides of the bent wiring board abut on the light receiving surface as the parallel surface.

17. The endoscope according to claim 12, wherein
the bent wiring board is inflexible.

18. The endoscope according to claim 12, wherein
the bent wiring board is flexible, and
an inner side of the bending section in the bent wiring board is filled with resin.

19. The endoscope according to claim 2, wherein
the image pickup module further comprises
a prism including an incidence surface on which light of the object image collected by the image pickup optical system is incident, a reflection surface on which the object image is reflected, and an emission surface from which light of the object image is emitted,
the wiring member includes a fourth wiring board including an eleventh main surface and a twelfth main surface opposing the eleventh main surface, and
the eleventh main surface in the fourth wiring board is disposed on the reflection surface in the prism, and the light emitting element is mounted on the twelfth main surface, and
the first angle and the second angle are defined by an inclination angle of the reflection surface to the emission surface.

20. The endoscope according to claim 19, wherein
the light emitting element is housed in a space formed by extending the incidence surface in the prism in an optical axis direction of the image pickup optical system.

* * * * *